(12) United States Patent
Kikuchi

(10) Patent No.: US 11,455,509 B2
(45) Date of Patent: Sep. 27, 2022

(54) CLEANING MANAGEMENT APPARATUS AND CLEANING MANAGEMENT METHOD

(71) Applicant: OLYMPUS CORPORATION, Tokyo (JP)

(72) Inventor: Kei Kikuchi, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 18 days.

(21) Appl. No.: 17/106,379

(22) Filed: Nov. 30, 2020

(65) Prior Publication Data

US 2021/0097365 A1 Apr. 1, 2021

Related U.S. Application Data

(63) Continuation of application No. PCT/JP2019/007056, filed on Feb. 25, 2019.

(30) Foreign Application Priority Data

May 31, 2018 (JP) .............................. JP2018-104966

(51) Int. Cl.
*G06M 1/00* (2006.01)
*G06M 1/08* (2006.01)
*A61B 1/00* (2006.01)
*A61B 1/12* (2006.01)

(52) U.S. Cl.
CPC ......... *G06M 1/083* (2013.01); *A61B 1/00004* (2013.01); *A61B 1/121* (2013.01)

(58) Field of Classification Search
CPC ..... G06M 1/083; A61B 1/00004; A61B 1/121

USPC ....................................................... 235/91 R
See application file for complete search history.

(56) References Cited

U.S. PATENT DOCUMENTS

| | | | |
|---|---|---|---|
| 2018/0102189 A1* | 4/2018 | Hosoi | G16H 40/20 |
| 2020/0260943 A1* | 8/2020 | Nishi | G02B 23/24 |

FOREIGN PATENT DOCUMENTS

| | | | |
|---|---|---|---|
| JP | 03-049730 A | 3/1991 | |
| JP | 10-309254 A | 11/1998 | |
| JP | 2007-325724 A | 12/2007 | |
| JP | 2009-131295 A | 6/2009 | |
| JP | 2012-239536 A | 12/2012 | |

(Continued)

OTHER PUBLICATIONS

International Search Report and International Preliminary Report on Patentability dated May 14, 2019 received in PCT/JP2019/007056.

(Continued)

*Primary Examiner* — Daniel A Hess
(74) *Attorney, Agent, or Firm* — Scully, Scott, Murphy & Presser, P.C.

(57) ABSTRACT

A cleaning management apparatus manages bedside cleaning for an endoscope connected to an examination apparatus. After an examination is completed, a measurement unit measures the operation time of a predetermined operation button of the endoscope. A recording control unit records that a preliminary cleaning has already been performed when the operation time that has been measured satisfies a completion condition. A notification unit gives notice of a message indicating that the preliminary cleaning is completed when the measured operation time satisfies the completion condition.

14 Claims, 4 Drawing Sheets

(56) References Cited

FOREIGN PATENT DOCUMENTS

| | | |
|---|---|---|
| JP | 2014-057753 A | 4/2014 |
| WO | 2016/009678 A1 | 1/2016 |

OTHER PUBLICATIONS

Japanese Office Action dated Apr. 6, 2021 received in 2020-521701.

\* cited by examiner

```
THREE MINUTES HAVE BEEN PASSED.
PLEASE PROMPTLY PERFORM THE REMAINING
TASKS OF THE BEDSIDE CLEANING.
```

<u>4</u>

CLEANING MANAGEMENT APPARATUS AND CLEANING MANAGEMENT METHOD

CROSS-REFERENCE TO RELATED APPLICATIONS

This application is based upon and claims the benefit of priority from the prior Japanese Patent Applications No. 2018-104966, filed on May 31, 2018, and International Application No. PCT/JP2019/007056, filed on Feb. 25, 2019, the entire contents of which are incorporated herein by reference.

BACKGROUND OF THE INVENTION

1. Field of the Invention

The present disclosure relates to a technology for managing preliminary cleaning of endoscopes.

2. Description of the Related Art

Patent Document 1 discloses a technology for reading identification information from an IC tag of an endoscope on which preliminary cleaning is to be performed, adding preliminary cleaning execution information to the read identification information so as to generate a preliminary cleaning history, and storing the preliminary cleaning history as cleaning history information in a cleaning history DB.

[Patent Document 1] Japanese Patent Application Publication NO. 2012-239536

In Japan, the Japan Gastroenterological Endoscopy Society published "Guidelines for Cleaning and Disinfecting Gastroenterological Endoscopy Equipment" in 1998, and in medical facilities, cleaning and disinfection are carried out in accordance with the published guidelines to prevent infection caused by endoscopic examination. In order to efficiently perform cleaning and disinfection of endoscopes, endoscope cleaning apparatuses that automatically perform a cleaning process, a disinfection process, and a rinsing process are used in many medical facilities.

If endoscope used in examinations are directly placed in a cleaning tank of an endoscope cleaning apparatus for cleaning, the mucus, blood, and the like of the patients may remain in the endoscopes. Therefore, the guidelines stipulate that endoscopes used in examinations should be preliminarily cleaned manually before being placed in a cleaning tank. Preliminary cleaning includes "bedside cleaning" where an endoscope removed from the patient is cleaned immediately after the examination while the endoscope is being connected to a light source apparatus (examination apparatus) and "manual cleaning" where the endoscope that has been bedside-cleaned is removed from the examination apparatus, placed in a dedicated container and carried into a cleaning room, and cleaned with a brush in a sink in the cleaning room.

The endoscope cleaning apparatus is equipped with a function of recording cleaning execution information such as cleaning details and cleaning time. Therefore, the cleaning execution information of an endoscope for which the endoscope cleaning apparatus has been used is automatically recorded in a cleaning history DB. Meanwhile, since the preliminary cleaning is manual cleaning, it is necessary to manually register the cleaning execution information of the preliminary cleaning in the cleaning history DB.

SUMMARY OF THE INVENTION

In this background, a purpose of the present disclosure is to provide a technique for efficiently registering cleaning execution information in preliminary cleaning in a cleaning history DB.

An embodiment of the present disclosure relates to a cleaning management apparatus for managing preliminary cleaning of an endoscope connected to an examination apparatus, including: a processor including hardware, wherein the processor is configured to: measure an operation time of a predetermined operation button of the endoscope after an examination is completed; and record that the preliminary cleaning has already been performed when the operation time that has been measured satisfies a completion condition. The preliminary cleaning is cleaning that is performed before automatic cleaning is performed by an endoscope cleaning apparatus.

Another embodiment of the present disclosure relates to a cleaning management method for managing preliminary cleaning of an endoscope connected to an examination apparatus, including: measuring an operation time of a predetermined operation button of the endoscope after an examination is completed; and recording that the preliminary cleaning has already been performed when the operation time that has been measured satisfies a completion condition.

Optional combinations of the aforementioned constituting elements and implementations of the present disclosure in the form of methods, apparatuses, systems, recording mediums, and computer programs may also be practiced as additional modes of the present disclosure.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

FIG. 5 is a diagram showing another example of a warning message.

DETAILED DESCRIPTION OF THE INVENTION

The invention will now be described by reference to the preferred embodiments. This does not intend to limit the scope of the present invention, but to exemplify the invention.

Figure 1:
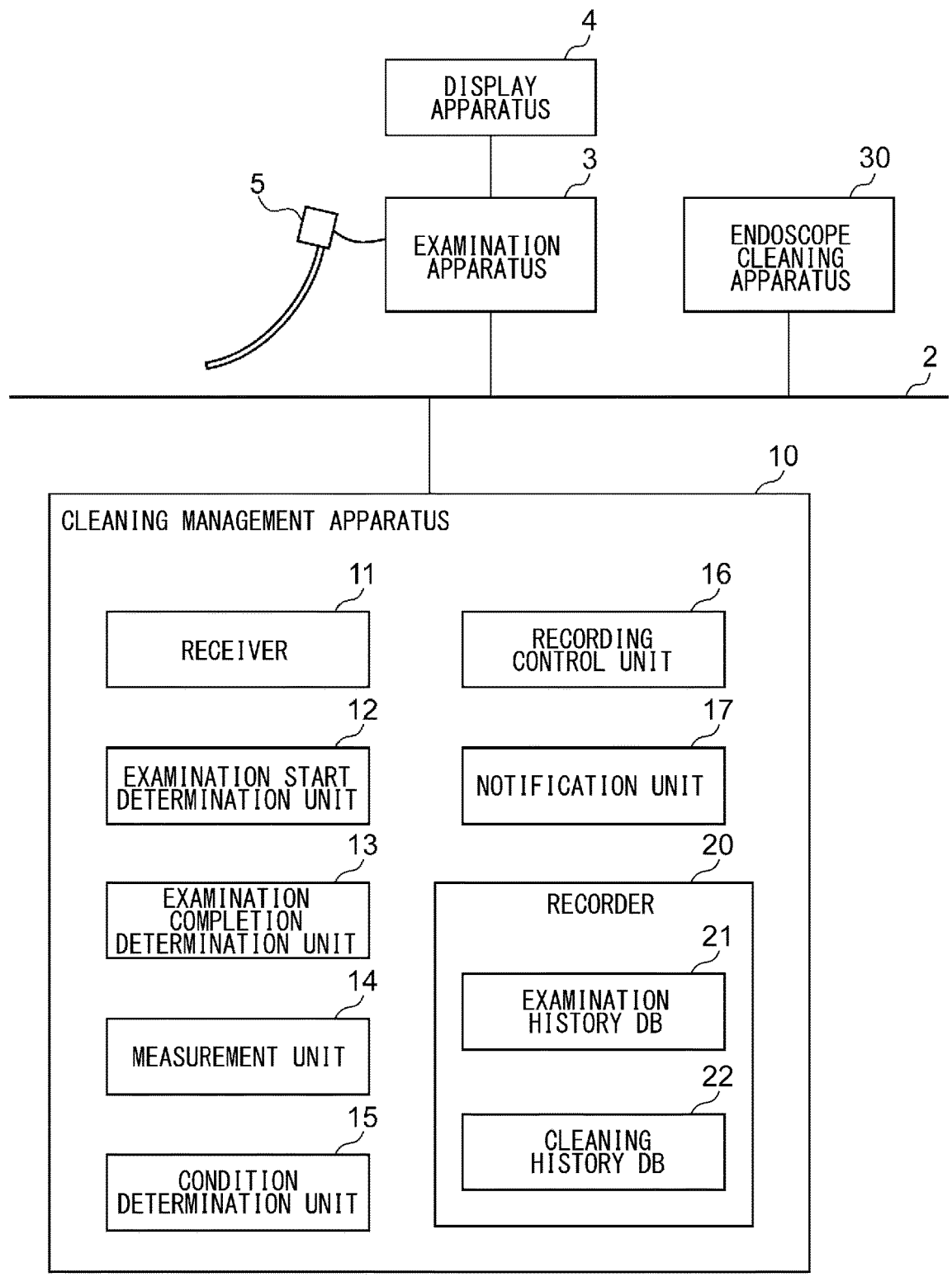
FIG. 1 is a diagram showing the configuration of a cleaning management system according to an embodiment.

FIG. 1 shows the configuration of a cleaning management system 1 according to an embodiment of the present disclosure. The cleaning management system 1 is a system for managing the preliminary cleaning of an endoscope 5 used in an examination and includes an examination apparatus 3, a display apparatus 4, a cleaning management apparatus 10, and an endoscope cleaning apparatus 30. The cleaning management apparatus 10 is communicably connected to the examination apparatus 3 and the endoscope cleaning apparatus 30 by a network 2 such as a local area network (LAN)

and receives various pieces of data and information from the examination apparatus 3 and the endoscope cleaning apparatus 30.

The cleaning management apparatus 10 includes a receiver 11, an examination start determination unit 12, an examination completion determination unit 13, a measurement unit 14, a condition determination unit 15, a recording control unit 16, a notification unit 17, and a recorder 20 and manages the preliminary cleaning of the endoscope 5 used in an examination. The recorder 20 has an examination history DB 21 for recording information related to the examination and a cleaning history DB 22 for recording cleaning execution information. The preliminary cleaning includes "bedside cleaning" and "manual cleaning". The cleaning management apparatus 10 according to the embodiment manages "bedside cleaning" for cleaning the endoscope 5 connected to the examination apparatus 3 and has a function of determining that bedside cleaning has been performed and automatically recording cleaning execution information in the cleaning history DB 22.

The configuration thereof is implemented by hardware such as an arbitrary processor, a memory, auxiliary storage, or other LSIs and by software such as a program or the like loaded into the memory. The figure depicts functional blocks implemented by the cooperation of hardware and software. Thus, a person skilled in the art should appreciate that there are many ways of accomplishing these functional blocks in various forms in accordance with the components of hardware only, software only, or the combination of both.

The examination apparatus 3 is connected to the endoscope 5 and provides a light source to the endoscope 5. Before the start of the examination, the nurse selects an examination to be performed from an examination list displayed on the display apparatus 4 or another display apparatus. When the endoscope 5 is connected, the examination apparatus 3 acquires identification information (scope ID) for identifying the endoscope 5 and transmits the scope ID and information for identifying the examination (examination ID) to the cleaning management apparatus 10.

When an examination start button provided on the examination apparatus 3 is operated, the examination apparatus 3 transmits operation information of the examination start button to the cleaning management apparatus 10. In the cleaning management apparatus 10, the receiver 11 receives the operation information of the examination start button, and the examination start determination unit 12 determines that the examination has been started. The examination start determination unit 12 may determine that the examination has been started when receiving a first captured image data transmitted from the examination apparatus 3 after the receiver 11 receives the operation information of the examination start button. When the examination start determination unit 12 determines that the examination has been started, the recording control unit 16 records data and information transmitted from the examination apparatus 3 in the examination history DB 21 as examination information.

The endoscope 5 is provided with various operation buttons such as a suction button, a water supply button, and an air supply button. The suction button is an operation button for sucking foreign substances or the like inside the body through a suction channel. The water supply button is an operation button for sending water into the body through a water supply channel. The air supply button is an operation button for sending gas into the body through an air supply channel. During the examination, the doctor operates the operation buttons as needed. The water supply button and the air supply button may be formed as one button unit.

The examination apparatus 3 processes image data acquired by the endoscope 5 and displays a captured image on the display apparatus 4. Further, the examination apparatus 3 acquires a captured image at the timing when a release switch of the endoscope is pressed and transmits the acquired captured image data to the cleaning management apparatus 10. During the examination, the recording control unit 16 records the captured image data transmitted from the examination apparatus 3 and the operation information of various operation buttons on the endoscope 5 in the examination history DB 21 as examination information.

When the endoscope 5 is removed from the patient's body and the examination completion button provided on the examination apparatus 3 is operated, the examination apparatus 3 transmits operation information of the examination completion button to the cleaning management apparatus 10. In the cleaning management apparatus 10, the receiver 11 receives the operation information of the operation completion button, and the examination completion determination unit 13 determines the completion of the examination. After the examination is completed, the measurement unit 14 measures the operation time of a predetermined operation button of the endoscope 5.

The "Guidelines for Cleaning and Disinfecting Gastroenterological Endoscopy Equipment" published in 1998 includes task details of "bedside cleaning" in which an endoscope 5 removed from the patient is cleaned while being connected to an examination apparatus 3 that provides a light source. Bedside cleaning includes the following tasks:

(Task 1) Clean the inside of the suction channel by sucking 200 ml or more of an enzyme detergent solution.

(Task 2) Clean the inside of the water supply channel.

(Task 3) Clean the inside of the air supply channel.

In Task 1, the operator puts the tip of the endoscope 5 into a tank containing an enzyme detergent solution, operates the suction button for a first predetermined time or longer, sucks the enzyme cleaning solution into the suction channel for cleaning, and removes body fluids including mucus, blood, and the like remaining inside the suction channel. The first predetermined time is set to a time during which 200 ml or more of the enzyme cleaning solution can be sucked, for example, 30 seconds.

In task 2, the operator operates the water supply button for a second predetermined time or longer to allow water to flow into the water supply channel. The operator points the tip of the endoscope 5 toward the inside of a container that receives water and puts water sent out from the tip into the container. In Task 3, the operator operates the air supply button for a third predetermined time or longer to allow the air to flow into the air supply channel. Further, in Task 3, the tip of the endoscope 5 is preferably directed toward the inside of the container that receives water, and Task 2 and Task 3 are carried out in succession. The second predetermined time and the third predetermined time may be appropriately set at the medical facility. For example, the second predetermined time may be 30 seconds, and the third predetermined time may be 10 seconds.

Since each task of the bedside cleaning is performed while the endoscope 5 connected to the examination apparatus 3, when a button provided on the endoscope 5 is operated, operation information thereof is transmitted to the cleaning management apparatus 10 from the examination apparatus 3 when the button is being operated. The cleaning management apparatus 10 according to the embodiment monitors the operation status of the various buttons after the examination is completed and determines whether or not a bedside cleaning completion condition is satisfied.

In the embodiment, the bedside cleaning completion condition is determined by the following Conditions 1 to 3.
(Condition 1) The suction channel has been cleaned.
(Condition 2) The water supply channel has been cleaned.
(Condition 3) The air supply channel has been cleaned.

Figure 2:
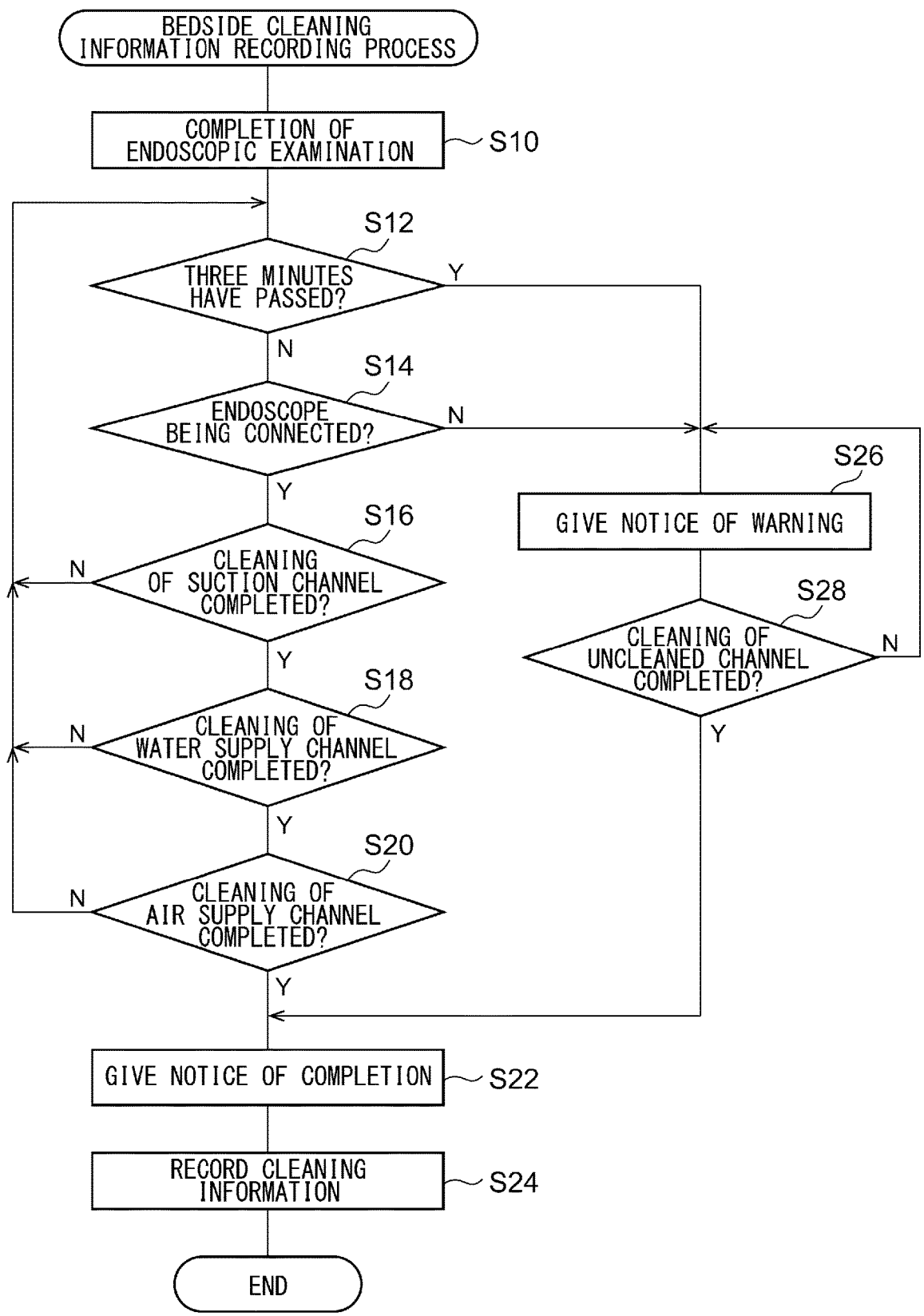
FIG. 2 is a diagram showing a flowchart for recording cleaning execution information.

FIG. 2 shows a flowchart for automatically recording bedside cleaning execution information. When the examination completion button of the examination apparatus 3 is operated, the receiver 11 receives the operation information of the operation completion button, and the examination completion determination unit 13 determines the completion of the examination (S10).

A bedside cleaning needs to be performed promptly after the examination is completed in order to remove the patient's mucus and blood. Therefore, when the examination is completed, the condition determination unit 15 sets a timer in order to determine the normal completion of the bedside cleaning and monitors whether the bedside cleaning is completed within a fourth predetermined time (S12). In the embodiment, the fourth predetermined time is set to 3 minutes, and if the bedside cleaning completion condition is not satisfied within 3 minutes, a warning is given to the operator (S26).

When the endoscope 5 used in the examination is connected to the examination apparatus 3 (Y in S14) before three minutes have passed after the completion of the examination (N in S12), the condition determination unit 15 determines whether or not the cleaning of the suction channel of the endoscope 5 is completed (S16).

In S16, when the receiver 11 receives the operation information of the suction button from the examination apparatus 3, the measurement unit 14 measures the operation time of the suction button. The condition determination unit 15 monitors the operation time of the suction button (N in S16), and when the operation time of the suction button is the first predetermined time (for example, 30 seconds) or more, the condition determination unit 15 determines that the cleaning of the suction channel of the endoscope 5 is completed (Y in S16).

Subsequently, the condition determination unit 15 determines whether or not the cleaning of the water supply channel of the endoscope 5 is completed (S18). In S18, when the receiver 11 receives the operation information of the water supply button from the examination apparatus 3, the measurement unit 14 measures the operation time of the water supply button. The condition determination unit 15 monitors the operation time of the water supply button (N in S18), and when the operation time of the water supply button is the second predetermined time (for example, 30 seconds) or more, the condition determination unit 15 determines that the cleaning of the water supply channel of the endoscope 5 is completed (Y in S18).

Subsequently, the condition determination unit 15 determines whether or not the cleaning of the air supply channel of the endoscope 5 is completed (S20). In S20, when the receiver 11 receives the operation information of the air supply button from the examination apparatus 3, the measurement unit 14 measures the operation time of the air supply button. The condition determination unit 15 monitors the operation time of the air supply button (N in S20), and when the operation time of the air supply button is the third predetermined time (for example, 10 seconds) or more, the condition determination unit 15 determines that the cleaning of the air supply channel of the endoscope 5 is completed (Y in S20). The order of S18 and S20 may be interchanged.

In this way, the measurement unit 14 measures the respective operation times of the plurality of operation buttons according to Conditions 1 to 3, and the condition determination unit 15 determines whether the measured operation times satisfy the completion condition of the bedside cleaning. The determination process by the condition determination unit 15 is performed before three minutes have passed after the completion of the examination (N in S12) and when the endoscope 5 is connected to the examination apparatus 3 (Y in S14). When the respective operation times of the plurality of operation buttons according to Conditions 1 to 3 satisfy the completion condition, the notification unit 17 notifies the operator of a message indicating that the bedside cleaning is completed in a normal manner (S22).

Figure 3:
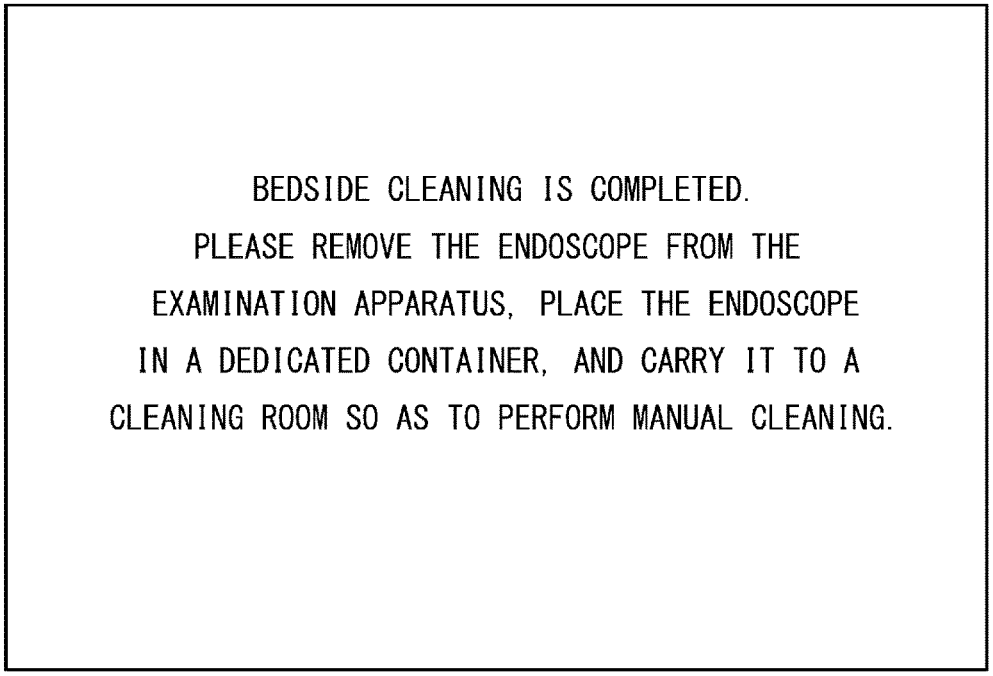
FIG. 3 is a diagram showing an example of a completion message.

FIG. 3 shows an example of a completion message displayed on the display apparatus 4. The completion message may be output by voice from the examination apparatus 3. Upon being notified of the completion of the bedside cleaning, the operator recognizes that the bed cleaning has been performed properly. After that, the operator removes the endoscope 5 from the examination apparatus 3, places the endoscope in a dedicated container, and carries the endoscope into the cleaning room.

Further, when the respective operation times of the plurality of operation buttons according to Conditions 1 to 3 satisfy the completion condition, the recording control unit 16 records that the preliminary cleaning has already been performed in the cleaning history DB 22 in association with the scope ID of the endoscope 5. As described above, according to the cleaning management apparatus 10 of the embodiment, the execution record of the bedside cleaning can be automatically registered in the cleaning history DB 22.

On the other hand, if the measured operation times do not satisfy the completion condition, the notification unit 17 notifies the operator of a warning message indicating that the preliminary cleaning has not been completed (S26). The timing of giving notice of the warning message may be when the endoscope 5 is removed from the examination apparatus 3 (N in S14). If the endoscope 5 is removed from the examination apparatus 3 before the operation times of the plurality of operation buttons satisfy the completion condition (N in S14), the notification unit 17 notifies the operator of a message indicating that the preliminary cleaning has not been completed (S26).

Figure 4:
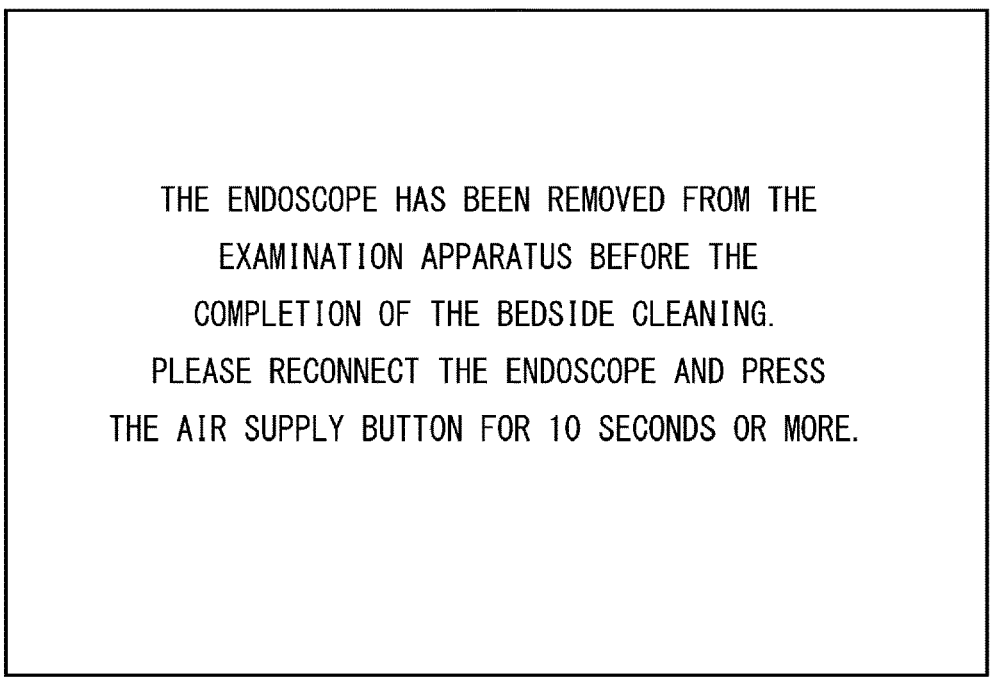
FIG. 4 is a diagram showing an example of a warning message.

FIG. 4 shows an example of a warning message displayed on the display apparatus 4. When displaying a warning message on the display apparatus 4, the notification unit 17 may output a warning sound such as a buzzer sound from a speaker of the examination apparatus 3 for the purpose of making the operator notice the message display. Further, in addition to being displayed on the display apparatus 4, the warning message may also be output by voice from the speaker. Upon being notified of the warning message, the operator recognizes that the bedside cleaning has not been performed properly. This warning message instructs the operator to reconnect the endoscope 5 to the examination apparatus 3 and press the air supply button for 10 seconds or longer. By informing, by the condition determination unit 15, the notification unit 17 of the reason why the completion condition for the bedside cleaning is not satisfied, the notification unit 17 can notify the operator of tasks to be additionally performed. For example, if the air supply button has been pressed for only seven seconds before the endoscope 5 is removed from the examination apparatus 3, the notification unit 17 may give notification of the shortage of the operation time as follows: "Please press the air supply button for three seconds or more".

After the endoscope 5 is reconnected to the examination apparatus 3, the condition determination unit 15 determines whether or not the cleaning of the uncleaned channel of the endoscope 5 is completed (S28). Preferably, the notification unit 17 continues to give notice of a warning message (S26) until the cleaning of the uncleaned channel is determined to have been completed (N in S28). When the condition determination unit 15 determines that the cleaning of the uncleaned channel of the endoscope 5 is completed (Y in S28), the notification unit 17 notifies the operator of a message indicating that the bedside cleaning is completed (S22), and the recording control unit 16 records in the cleaning history DB 22 that the bedside cleaning has already been performed (S24).

In the embodiment, the step S12 is provided in order to request the operator to perform the bedside cleaning promptly. If three minutes have elapsed before the respective operation times of the plurality of operation buttons satisfy the completion condition (Y in S12), the notification unit 17 notifies the operator of a message indicating that the preliminary cleaning has not been completed (S26). The notification unit 17 may display the message on the display apparatus 4 and output a buzzer sound from the speaker. Further, in addition to being displayed on the display apparatus 4, the message may also be output by voice from the speaker.

FIG. 5 shows another example of a warning message displayed on the display apparatus 4. The warning message may be output by voice from the examination apparatus 3. Upon being notified of the warning message, the operator recognizes that the operator needs to hurry. After that, when the condition determination unit 15 determines that the cleaning of the uncleaned channel of the endoscope 5 is completed (Y in S28), the notification unit 17 notifies the operator of a message indicating that the bedside cleaning is completed (S22), and the recording control unit 16 records in the cleaning history DB 22 that the bedside cleaning has already been performed (S24).

The recording control unit 16 may not be able to record information in the cleaning history DB 22 in a normal manner due to the occurrence of an abnormality such as a memory failure of the endoscope cleaning apparatus 30. The recording control unit 16 may stop recording the information and cancel the cooperation with the endoscope cleaning apparatus 30 at the moment when the information indicating the abnormality is sent from the endoscope cleaning apparatus 30. Further, if necessary, the recording control unit 16 may delete the information already recorded in the cleaning history DB 22. At this time, the notification unit 17 may notify the operator of a message indicating that an abnormality has occurred. This message may indicate "An abnormality has occurred in the endoscope cleaning apparatus, and information cannot be recorded normally. Please contact the manufacturer."

Similarly, the recording control unit 16 may not be able to record information in the examination history DB 21 in a normal manner due to the occurrence of an abnormality such as a memory failure of the examination apparatus 3. The recording control unit 16 may stop recording the information and cancel the cooperation with the examination apparatus 3 at the moment when the information indicating the abnormality is sent from the examination apparatus 3. Further, if necessary, the recording control unit 16 may delete the information already recorded in the examination history DB 21. At this time, the notification unit 17 may notify the operator of the same message as those notified at the time of the occurrence of an abnormality in the cleaning apparatus.

Described above is an explanation on the present disclosure based on the embodiments. These embodiments are intended to be illustrative only, and it will be obvious to those skilled in the art that various modifications to constituting elements and processes could be developed and that such modifications are also within the scope of the present disclosure.

What is claimed is:

1. A cleaning management apparatus for managing preliminary cleaning of an endoscope connected to an examination apparatus, the cleaning management apparatus comprising:
   a processor comprising hardware, wherein the processor is configured to:
      determine completion of an examination of the endoscope in a patient;
      after the examination is determined to be complete, measure respective operation times of a plurality of operation buttons of the endoscope while the endoscope is connected to the examination apparatus, which is used for the examination, the plurality of operation buttons including at least a suction button, a water supply button, and an air supply button; and
      while the endoscope remains connected to the examination apparatus and after the examination is determined to be complete, record that the preliminary cleaning has already been performed when the measured operation times satisfy a completion condition.

2. The cleaning management apparatus according to claim 1, wherein the processor is configured to give notice of a message indicating that the preliminary cleaning is completed when the measured operation times satisfy the completion condition.

3. The cleaning management apparatus according to claim 1, wherein the processor is configured to give notice of a message indicating that the preliminary cleaning has not been completed when the measured operation times do not satisfy the completion condition.

4. The cleaning management apparatus according to claim 3, wherein the processor is configured to give notice of a message when the endoscope is removed from the examination apparatus.

5. The cleaning management apparatus according to claim 3, wherein the processor is configured to give notice of a message after a predetermined time has passed after the completion of the examination.

6. The cleaning management apparatus according to claim 1, wherein where the operation times fail to satisfy the completion condition within a predetermined time period of when the determination that the examination is complete, the processor is further configured to give notice of a message indicating that the preliminary cleaning is not completed.

7. The cleaning management apparatus according to claim 1, wherein where the endoscope is disconnected from the examination apparatus subsequent to the determination that the examination is complete and prior to the operation times satisfying the completion condition, the processor is further configured to give notice of a message indicating that the preliminary cleaning is not completed.

8. A cleaning management method for managing preliminary cleaning of an endoscope connected to an examination apparatus, the cleaning management method comprising:
   determine completion of an examination of the endoscope in a patient;

after the examination is determined to be complete, measuring respective operation times of a plurality of operation buttons of the endoscope while the endoscope is connected to the examination apparatus, which is used for the examination, the plurality of operation buttons including at least a suction button, a water supply button, and an air supply button; and while the endoscope remains connected to the examination apparatus and after the examination is determined to be complete, recording that the preliminary cleaning has already been performed when the measured operation times satisfy a completion condition.

9. The cleaning management method according to claim 8, further comprising:
giving notice of a message indicating that the preliminary cleaning is completed when the measured operation times satisfy the completion condition.

10. The cleaning management method according to claim 8, further comprising:
giving notice of a message indicating that the preliminary cleaning is not completed when the measured operation times do not satisfy the completion condition.

11. The cleaning management method according to claim 10, wherein in the giving notice, notice of a message is given when the endoscope is removed from the examination apparatus.

12. The cleaning management method according to claim 10, wherein in the giving notice, notice of a message is given after a predetermined time has passed after the completion of the examination.

13. The cleaning management method according to claim 8, further comprising, where the operation times fail to satisfy the completion condition within a predetermined time period of when the determination that the examination is complete, giving notice of a message indicating that the preliminary cleaning is not completed.

14. The cleaning management method according to claim 8, further comprising, where the endoscope is disconnected from the examination apparatus subsequent to the determination that the examination is complete and prior to the operation times satisfying the completion condition, giving notice of a message indicating that the preliminary cleaning is not completed.

* * * * *